US00PP28026P3

(12) United States Plant Patent
Hoogendoorn

(10) Patent No.: US PP28,026 P3
(45) Date of Patent: May 16, 2017

(54) ***MILTONIDIUM* ORCHID PLANT NAMED 'CAMBOLYK'**

(50) Latin Name: *Nothogenus:×Miltonidium*
Varietal Denomination: CAMBOLYK

(71) Applicant: ANTHURA B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 79 days.

(21) Appl. No.: 14/545,659

(22) Filed: Jun. 3, 2015

(65) Prior Publication Data

US 2016/0360673 P1 Dec. 8, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Upov Pluto Plant Variety Database Sep. 24, 2016 retrieved on Sep. 29, 2016, retrieved from the Internet at <https://www3.wipo.int/pluto/user/en/index.jsp> one page.*
EU Community Plant Variety Rights Application No. 2014/0815, Application n°A201403387, filed Mar. 24, 2014, 7 pages.
EU Community Plant Variety Office Official Gazette, Mar. 2014, Jun. 15, 2014, cover page and pp. 30, 50.

* cited by examiner

*Primary Examiner* — June Hwu
(74) *Attorney, Agent, or Firm* — Jondle & Associates, P.C.

(57) ABSTRACT

A new and distinct variety of ×*Miltonidium* plant named 'CAMBOLYK', particularly characterized by having dark red flowers, 1-4 peduncles, a peduncle that is medium and sturdy, leaves that are lanceolate and moderately to very elongated, and is propagated by tissue culture is disclosed.

3 Drawing Sheets

Genus and species: Nothogenus: ×*Miltonidium*.
Variety denomination: 'CAMBOLYK'.

BACKGROUND OF THE NEW PLANT

The present invention comprises a new and distinct cultivar of ×*Miltonidium* plant, botanically known as ×*Miltonidium* of the Orchidaceae family, and hereinafter referred to by the cultivar name 'CAMBOLYK'.

Miltonia, Odontoglossum, Oncidium and Brassia and some other genera are a complex group of orchid species that are easily hybridized. The boundaries between the genera have been under discussion for the last several decades. According to the most recent classification by Pridgeon, Cribb, Chase and Rasmussen (Genera Orchidacearum), the plant herein described is most likely a complex hybrid between Miltonia and Oncidium species, hence called a ×*Miltonidium*

All ×*Miltonidium* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth); two leaves on each side. The peduncles vary in size from 20-70 cm.

×*Miltonidium* orchids are used as flowering potted-plants for home or interiorscape. ×*Miltonidium* produces upright or pendent lateral racemes or panicles, often with many showy flowers which open in succession beginning with the lowermost. The flowers possess three sepals and two petals; the lateral ones being alike. Flower colors include various shades of pink, white, yellow, and red-brown.

×*Miltonidium* orchids are typically propagated from tissue culture. Asexual propagation of ×*Miltonidium* is often done from off-shoots which arise from the lower bracts of the inflorescence. The resulting plants are detached from the mother plants and may be planted in a suitable substrate.

The new ×*Miltonidium* 'CAMBOLYK' is particularly characterized by its attractive and unique dark red flowers, economical propagation by tissue culture, early flowering, and a plant dimension suitable for packaging and shipping to the market.

'CAMBOLYK' is a product of a planned breeding program conducted by the inventor in Bleiswijk, The Netherlands.

The new ×*Miltonidium* 'CAMBOLYK' originated from a cross made by the inventor in January 2005 in Bleiswijk, The Netherlands. The female parent is an orange ×*Miltonidium* pot plant named '60000-0149' (unpatented) and the male parent is a greyed-purple *Onicidium* pot plant named '60000-0165' (unpatented). A single plant was selected in April 2008 and has been asexually reproduced repeatedly by meristem tissue culture in Bleiswijk, The Netherlands over a 4-year period. The new variety has been found to retain its distinctive characteristics through successive asexual propagations.

Asexual reproduction of 'CAMBOLYK' by tissue culture was first performed in March 2011 in Bleiswijk, The Netherlands and has demonstrated that the new cultivar is firmly fixed and retained through successive generations of asexual reproduction.

Plant Breeder's Rights for this variety have been applied for in Europe on Mar. 24, 2014. 'CAMBOLYK' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Dark red flowers;
2) 1-4 peduncles;
3) Peduncle is medium and sturdy;
4) The shape of the leaf is lanceolate and is moderately to very elongated; and
5) Plants are propagated by meristem tissue culture.

DESCRIPTION OF THE PHOTOGRAPHS

This new ×*Miltonidium* plant is illustrated by the accompanying photographs which show the overall plant habit including blooms, buds and foliage of the plant; the colors shown are as true as can be reasonably obtained by conventional photographic procedures. The photographs are of a 40-week old plant grown in a greenhouse in Bleiswijk, The Netherlands in December 2014.

DESCRIPTION OF THE NEW VARIETY

Figure 1:
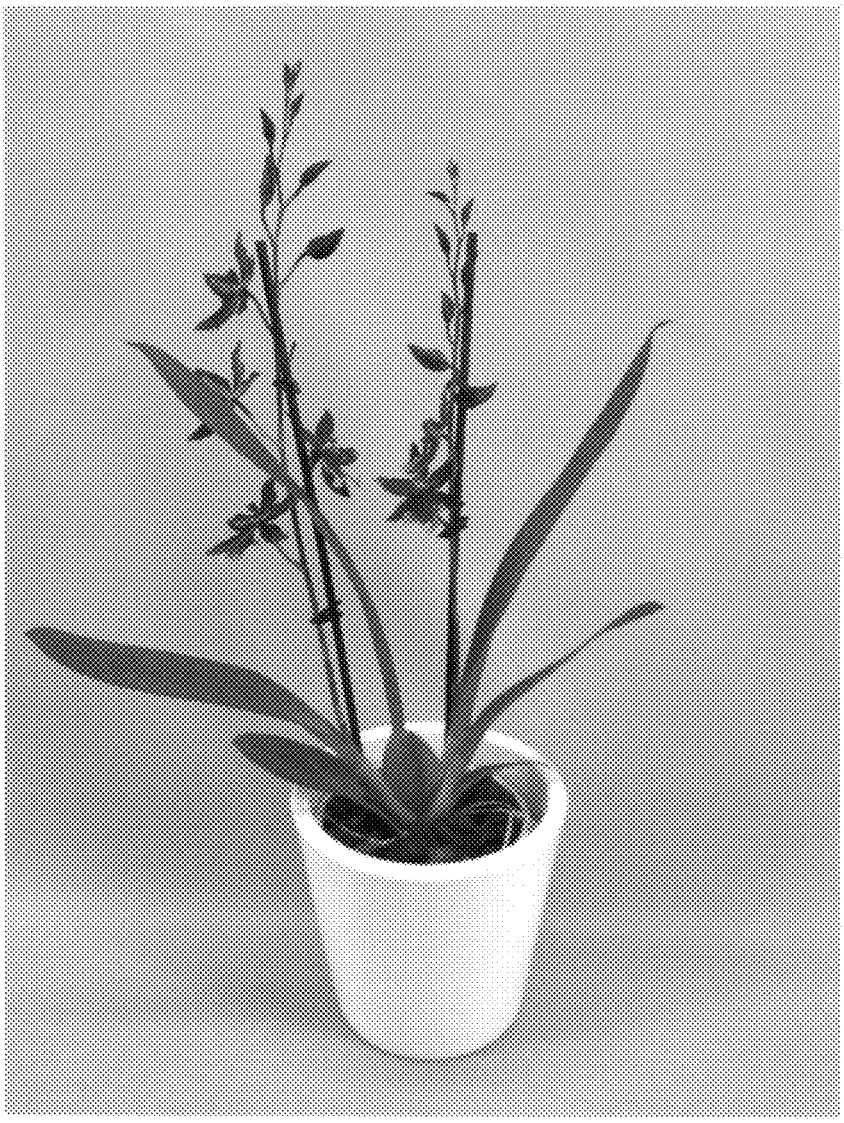
FIG. 1 shows the overall plant habit, including blooms, buds and foliage of 'CAMBOLYK'.
Figure 2:
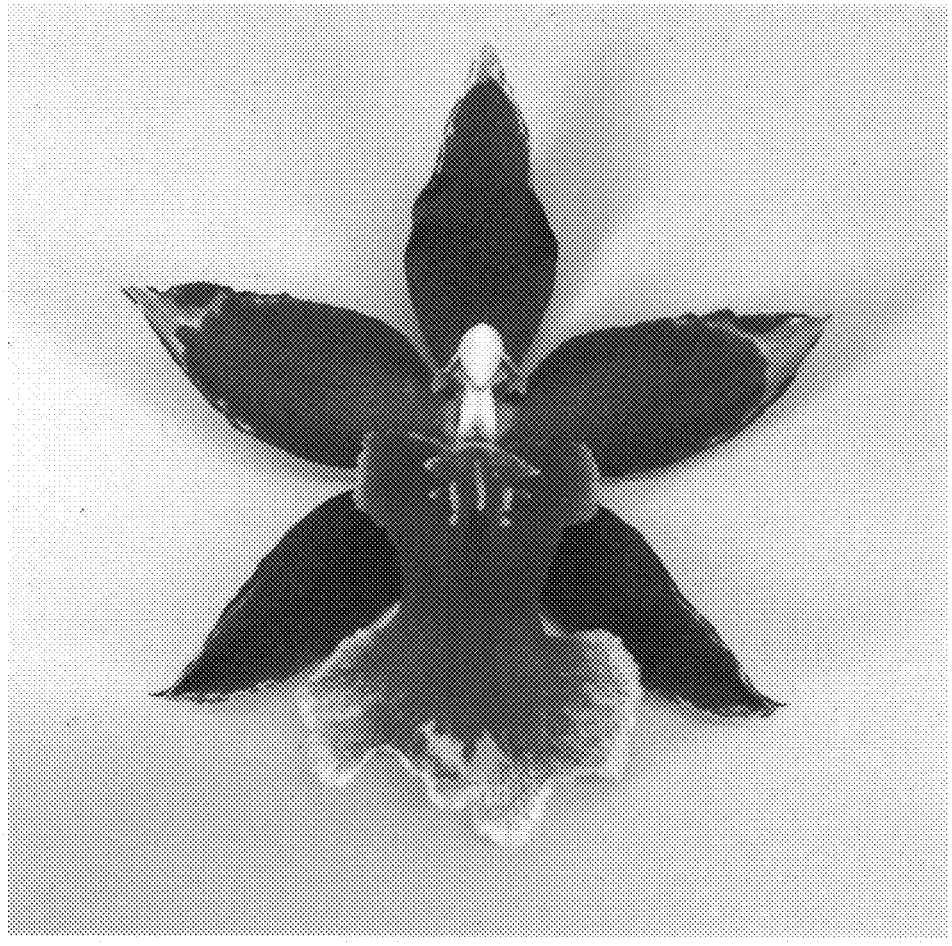
FIG. 2 shows a close-up of a flower of 'CAMBOLYK'.
Figure 3:
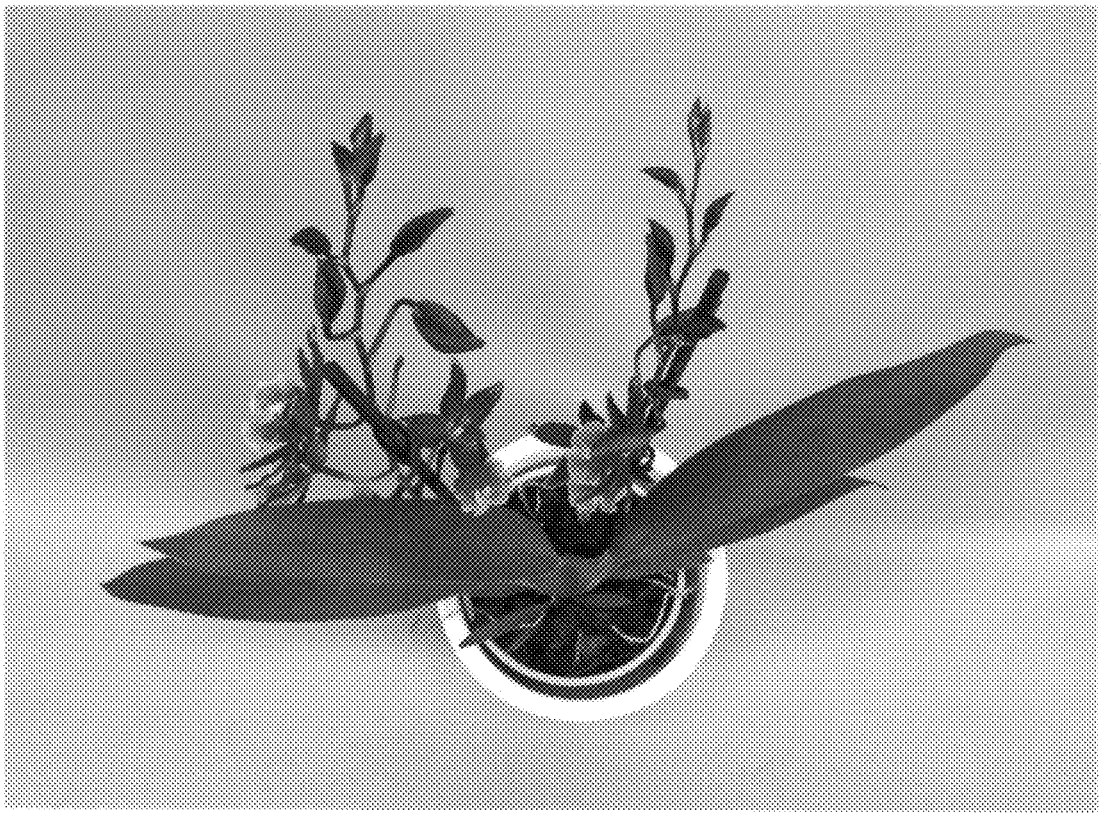
FIG. 3 shows a top view of the leaves of 'CAMBOLYK'.

The following detailed description sets forth the distinctive characteristics of 'CAMBOLYK'. The data which define these characteristics were collected from asexual reproductions carried out in Bleiswijk, The Netherlands. The plant history was taken on 40-week old plants which were planted from tissue culture in 12 centimeter pots and grown in a greenhouse between 20° C. to 25° C. for 40 weeks. Observations were made in December 2014. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—×*Miltonidium*.
- *Common name*.—Cambria.
- *Variety name*.—'CAMBOLYK'.

Parentage:
- *Female parent*.—×*Miltonidium* cultivar '60000-0149' (unpatented).
- *Male parent*.—Oncidium cultivar '60000-0165' (unpatented).

Propagation:
- *Type*.—Tissue culture.

Plant:
- *Crop time* (*time to produce a finished flowering plant*) .—40 to 50 weeks for a 12 cm pot.
- *Growth habit of peduncle*.—Sympodial.
- *Height* (*including pot, including inflorescence*).—45.0 cm to 55.0 cm.
- *Average plant spread*.—15.0 cm to 25.0 cm.
- *Vigor*.—Moderate.

Roots:
- *Root description*.—White/light green colored roots lightly branching with light growing tips (The exact shades of white may vary with minimal changes of environmental conditions).

Pseudobulb:
- *Number of pseudobulbs*.—1.
- *Shape*.—Laterally compressed ovoid.
- *Height*.—6.0 cm to 6.5 cm.
- *Length*.—3.0 cm to 3.5 cm.
- *Width*.—1.4 cm to 1.8 cm.
- *Color*.—Green (RHS 146A).

Leaves:
- *Mature leaves*.—Quantity per plant: 4 to 6 leaves are produced before flowering. Length (fully expanded): 24.0 cm to 26.0 cm. Width: 2.9 cm to 3.4 cm. Shape: Lanceolate. Base shape: Moderately elongated. Apex: Acute. Leaf margin: Entire. Color: Upper surface: RHS 146A. Lower surface: RHS 146B. Texture (upper and lower surfaces): Smooth. Thickness: 0.45 mm to 0.55 mm. Venation: Pattern: Parallel. Color of the midvein: Upper surface: RHS 146A. Lower surface: RHS 146B.

Peduncle:
- *Quantity per plant*.—1 to 4.
- *Number of flowers per peduncle*.—10 to 14.
- *Length*.—34.0 cm to 39.0 cm.
- *Diameter*.—3.0 mm to 3.5 mm.
- *Strength*.—Moderate.
- *Aspect*.—Upright.
- *Texture*.—Smooth.
- *Color*.—Green/greyed-brown (RHS 146A and 199A).
- *Internode length*.—40.0 mm to 50.0 mm.
- *Number of branches*.—0 to 1.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 170.0 mm to 220.0 mm.
- *Flowering time*.—First flowers can be expected 4 to 6 months after planting in a 12 cm pot.
- *Flower*.—Height: 54.0 mm to 59.0 mm. Diameter: 48.0 mm to 53.0 mm.
- *Flower longevity*.—On the plant: 5 to 10 weeks.
- *Fragrance*.—Present (Slight fragrance).
- *Petals*.—Shape: Ovate. Apex: Acute. Margin: Entire. Length (from base to tip): 22.0 mm to 25.0 mm. Width: 9.0 mm to 11.0 mm. Color (when fully opened): Upper surface: Basic color: Dark red (RHS 183A and 187A). Over color: Greyed-green tips (RHS 197D). Lower surface: Basic color: Dark red (RHS 183A and 187A). Over color: Greyed-green tips (RHS 195A).

Dorsal sepal:
- *Shape*.—Elliptic.
- *Margin*.—Entire.
- *Length* (*from base to tip*).—24.0 mm to 26.0 mm.
- *Width*.—8.0 mm to 10.0 mm.
- *Color* (*when fully opened*).—Upper surface: Basic color: Dark red (RHS 183A and 187A). Over color: Greyed-green tips (RHS 197D). Lower surface:

Basic color: Dark red (RHS 183A and 187A). Over color: Greyed-green tips (RHS 195A).

Lateral sepals:

*Shape*.—Ovate.

*Margin*.—Entire.

*Length* (*from base to tip*).—28.0 mm to 30.0 mm.

*Width*.—6.0 mm to 9.0 mm.

*Color* (*when fully opened*).—Upper surface: Basic color: Dark red (RHS 183A and 187A). Over color: Greyed-green tips (RHS 197D). Lower surface: Basic color: Dark red (RHS 183A and 187A). Over color: Greyed-green tips (RHS 195A).

Labellum (lip):

*Length*.—28.0 mm to 33.0 mm.

*Width*.—25.0 mm to 29.0 mm.

Lateral lobe:

*Average size*.—Medium.

*Shape*.—Not describable.

*Apex margin*.—Undulated.

*Color*.—Upper surface: Dark red (RHS 59A). Lower surface: Dark red (RHS 59B) and white towards the base (RHS NN155C).

Apical lobe:

*Average size*.—Medium.

*Shape*.—Not describable.

*Apex margin*.—Undulated.

*Color*.—Upper surface: Red-purple (RHS 71A and 59B) and white (RHS NN155C) towards the edge. Lower surface: Red-purple (RHS 61A and 59B) and slightly white (RHS NN155C) towards the edge.

Callus:

*Average size*.—Medium to large.

*Average number of protuberance*.—3 to 5.

*Shape*.—Not describable.

*Color*.—Dark red at the base (RHS 183A and 187B); yellow tips (RHS 12A/12B).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 7.0 mm to 9.0 mm. Diameter: 2.0 mm, toward the top 4.0 mm.

*Wings*.—Size: Not describable. Shape: Not describable.

*Color*.—Upper part greyed-purple (RHS 187A); lower part white/yellow (RHS 155C, 4C).

Pollinia:

*Quantity*.—2.

*Diameter*.—0.6 mm to 0.7 mm.

*Color*.—Yellow-orange (RHS 20A).

Ovary:

*Length*.—8.0 mm to 9.0 mm.

*Diameter*.—2.0 mm to 2.2 mm.

Pedicel:

*Length*.—29.0 mm to 31.0 mm.

*Diameter*.—2.1 mm to 2.3 mm.

*Texture*.—Smooth.

*Color*.—Green at the base (RHS 146C) and dark red towards the flower (RHS 187A).

Anther cap:

*Average size*.—1.0 mm to 3.0 mm.

*Shape*.—Oval cup shape.

*Color*.—Light yellow-green, almost white (RHS 155C).

Disease, pest, and stress resistance: No specific resistance or susceptibility observed.

Temperature tolerance: Not observed.

COMPARISON WITH PARENTAL AND COMMERCIAL VARIETIES

'CAMBOLYK' differs from female parent '60000-0149' (unpatented) in that 'CAMBOLYK' has dark red flowers, whereas '60000-0149' has orange flowers.

'CAMBOLYK' differs from male parent '60000-0165' (unpatented) in that 'CAMBOLYK' has larger flowers than '60000-0165'. Additionally, 'CAMBOLYK' has a peduncle that is green and greyed-brown and a petal and sepal margin that is entire, whereas '60000-0165' has a peduncle that is green and a petal and sepal margin that is undulated.

'CAMBOLYK' differs from commercial variety 'LAZIO' (unpatented) in that 'CAMBOLYK' has a smaller plant with only 1 or no branches, whereas 'LAZIO' has a larger plant with about 4 branches.

I claim:

1. A new and distinct variety of ×*Miltonidium* plant named 'CAMBOLYK', substantially as described and illustrated herein.

* * * * *